United States Patent [19]
Karlsson et al.

[11] Patent Number: 6,046,814
[45] Date of Patent: Apr. 4, 2000

[54] ADDITIONAL FEATURE FOR A MEASURING SENSOR USED IN THE SPECTROSCOPIC ANALYSIS OF MEDIUMS

[75] Inventors: Kai Karlsson, Helsinki; Kurt Peter Weckström, Espoo, both of Finland

[73] Assignee: Instrumentarium Oy, Helsinki, Finland

[21] Appl. No.: 08/919,745

[22] Filed: Aug. 28, 1997

[30] Foreign Application Priority Data

Aug. 30, 1996 [FI] Finland ..................................... 963388

[51] Int. Cl.⁷ .............................. G01J 5/08; G01N 21/84
[52] U.S. Cl. ...................................... 356/437; 250/339.13
[58] Field of Search .................................... 356/246, 439, 356/440, 437; 250/343, 339.13

[56] References Cited

U.S. PATENT DOCUMENTS

| | | |
|---|---|---|
| 3,745,349 | 7/1973 | Liston . |
| 4,468,561 | 8/1984 | Speeter . |
| 4,567,366 | 1/1986 | Shinohara .......................... 250/339.13 |
| 4,893,934 | 1/1990 | Hansen . |
| 5,254,858 | 10/1993 | Wolfman et al. . |
| 5,319,200 | 6/1994 | Rosenthal et al. . |

FOREIGN PATENT DOCUMENTS

| | | |
|---|---|---|
| 618465 | 10/1994 | European Pat. Off. . |
| 670486 | 9/1995 | European Pat. Off. . |
| 941001 | 9/1995 | Finland . |
| 101428 | 12/1995 | Finland . |
| 1592165 | 6/1987 | France . |
| 32 43 776 | 5/1984 | Germany . |
| 41 16 431 | 11/1992 | Germany . |
| 2249389 | 5/1992 | United Kingdom . |
| 2276003 | 9/1994 | United Kingdom . |

OTHER PUBLICATIONS

A Reliable, Accurate $CO_2$ Analyzer for Medical Use, Rodney J. Solomon, Hewlett–Packard Journal, Sep. 1961, pp. 3–9.

Primary Examiner—Frank G. Font
Assistant Examiner—Zandra V. Smith
Attorney, Agent, or Firm—Andrus, Sceales, Starke & Sawall

[57] ABSTRACT

The invention relates to an additional feature for use in a measuring sensor which is used for analyzing mediums spectroscopically. The measuring sensor comprises: a radiation source (1), emitting radiation which travels through a first window (3a) of a sample chamber (2), an absorption length (L1) and further a second window (3b) of the sample chamber (2), the sample chamber being provided, if necessary, with flow connections for a gas mixture; at least done detector (9), which is optically directed towards the second window; at least one optical filter (8), which is permeable to a certain wavelength band, or a radiation dispersion device between the radiation source and the detector. Between the first sample chamber window and the radiation source, the feature comprises a length (L2) and/or, between the second window and the detector, a length (L3), totalling at least about 20% of the absorption length. The length (L2) between an inner surface (13a) of the first sample chamber window and the radiation source and/or the length (L3) between an inner surface (13b) of the second window and the detector or, respectively, detectors are constituted over substantially all other sections of the radiation path, except those in alignment with possible accessories, by a solid material (7) transmissive to the applied radiation wavelengths. This material is preferably homogeneous at least in the direction transverse to a main radiating direction (R).

25 Claims, 4 Drawing Sheets

ADDITIONAL FEATURE FOR A MEASURING SENSOR USED IN THE SPECTROSCOPIC ANALYSIS OF MEDIUMS

BACKGROUND OF THE INVENTION

The present invention relates to an additional feature for use in a measuring sensor for the spectroscopic analysis of mediums, said measuring sensor comprising: a sample chamber for a gas mixture to be analyzed, which chamber is provided with flow connections for the flow-through of the gas mixture as well as with at least two windows transmissive to applied radiation, the inside surfaces of said windows defining therebetween a measuring absorption length; a radiation source for emitting radiation which progresses through the first window, the absorption length of the sample chamber, and further through the second window; one or a plurality of detectors which is or are optically directed towards this second window; at least one filter permeable to a certain wavelength band, or a radiation-dispersion producing means between the radiation source and each detector; as well as between the inside surface of the first sample chamber window and the radiation source a first length and/or between the inside surface of the second window and the detector or, respectively, detectors a second length, said lengths being in total at least about 20% of said absorption length. The invention relates also to a similar additional feature in a measuring sensor employing two or more filter-detector pairs. The invention relates also to a method for manufacturing such an additional feature for a light guide, comprising a housing which is made of a rigid material and includes radiation-transmitting ends and inner volume as well as a radiation-restricting inner surface and has a length which is at least about one and a half times over its mean diameter.

Figure 6:
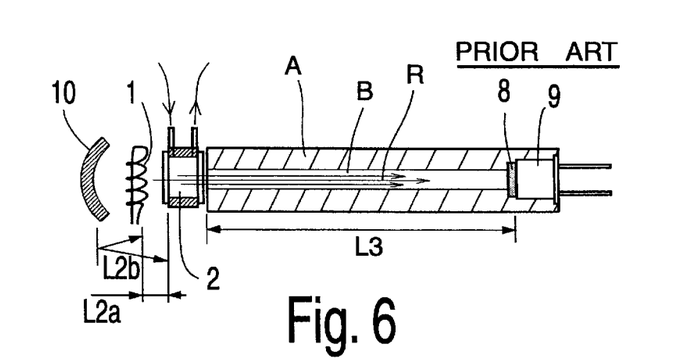
FIG. 6 shows a prior art measuring sensor applicable for measuring the concentration of a single gas component and not including an additional feature of the invention.

The above type of measuring sensors for the spectroscopic analysis of mediums have been disclosed e.g. in patents FI-95322, U.S. Pat. No. 5,254,858, U.S. Pat. No. 3,745,349, U.S. Pat. No. 4,468,561 and in the publication HEWLETT-PACKARD JOURNAL: R. J. Solomon—"A Reliable, Accurate $CO_2$ Analyzer for Medical Use", September 1981. FIG. 6 in the present application illustrates a basic principle for such a device based on infrared absorption and used for analyzing gas mixtures, corresponding primarily to the design described in the publication FI-95322. This analyzer consists of the following basic components: a radiation source 1, a possible mirror 10, and a sample chamber 2 as well as one or a plurality of infrared detectors 9 and, between these detectors and the radiation source, in this case an optical bandpass filter 8. This makes for a non-dispersive measuring system for measuring a radiation R having passed through the sample chamber 2 for an absorption caused by a given gas component. In the case of FIG. 6, the spacing between the sample chamber 2 and the filter 8 and the detector 9 comprises a wave tube A, just like in FI patent 95322, said tube having a length L3 and producing a roughly parallel beam of rays R to the filter 8, in this case an interference filter. It is also prior known to employ various optical components, such as lenses, concentrators, and the like, between the radiation source 1 and the sample chamber 2 and/or between the sample chamber 2 and the filter-detector assembly 8, 9. The non-dispersive measuring system obtained by means of a filter or filters can be replaced with a lattice or grid distributing the radiation into various wavelengths for providing a dispersive measuring system. The non-dispersive measuring system can also be provided, not only with a plurality of parallel-connected filter-detector assemblies, but also with a single detector and replaceable filters. However, a drawback in all these above-cited publications is that at some point between the radiation source 1 and the sample chamber 2 and/or between the sample chamber 2 and the detector 9 there is a substantial space which is more or less freely accessible for the external atmosphere. As a result of this, the composition of the external atmosphere can have an effect on the measuring result. This could even be a major effect, particularly when measuring some gas component which is also present in the ambient atmosphere. Thus, in the prior art technology depicted e.g. in FIG. 6, a wave tube A includes an interior B which, due to its length, may cause a substantial absorption in a radiation R traveling therethrough. This problem is indeed recognized in the patent FI-95322 and, in order to correct it, it has been proposed that the wave tube interior B be filled with vacuum or with a gas that does not absorb on the wavelengths used in measuring. Another proposed alternative is that the wave tube interior be provided with a suitable absorbent, such as silica gel, zeolite, activated carbon, or calcium hydroxide. However, such a solution requires that the wave tube in question be sealed absolutely hermetically, which in practice has proved highly difficult in terms of achieving an absolutely reliable result. The amount and, if necessary, also the replacement of absorbent also makes for a more complicated structure and operation. This problem, i.e. faulty absorption occurring in the path of radiation away from the sample chamber, is not mentioned at all in the other above-cited publications. However, this possibility of faulty absorption exists in all constructions set forth in the cited publications. Furthermore, in actual real-life measuring equipment, the path of radiation includes several locations, besides the above-mentioned optional wave tube, in which this faulty absorption may occur.

The above-described faulty absorption caused by the ambient atmosphere may occur over any such section of an optical path extending from a radiation source to a detector, which is exposed to this external gas. Thus, in the prior art shown in FIG. 6, faulty absorption may occur over a length L3 between the sample chamber window facing away from the radiation source and the detector, in this case over a length L2a between the non-encapsulated radiation source and the sample chamber window facing the same, as well as over a double length L2b extending from the radiation source via a mirror 10 back to the sample chamber window.

The patent application FI-942547 describes a measuring sensor consisting of a measuring rod, wherein some of the radiation path is designed by using e.g. a sapphire rod with a totally reflective outer surface or a bundle of fibers, as long as it comprises a tube permeable to reflecting inwards the applied wavelength. However, neither does this publication pay any attention to the above-described possibility of faulty absorption since the publication mentions, as an equal alternative to the above rod or fiberoptics, also an internally reflective tube exactly like in FIG. 6 depicting the prior art. Indeed, the only purpose of such rod-shaped, tubular, or fiberoptics is, as explained in the cited publication, to enable the accommodation of a measuring gap in a large-diameter channel inside the same through an opening in the wall as well as to enable the measuring gap surfaces to remain warm and, thus, to prevent the moisture possibly present in the large flow channel from condensing on the measuring gap surfaces. The construction described in the publication is only good for measuring the concentration of a single gas component, since the channel can only be fitted with a measuring rod having a very small cross-sectional area. Since, in the cited construction, the measuring gap has a very small maximum length, this results in a factor limiting the selection of the absorption length of measuring. It should also be noted that, if, as suggested in this publication, the structure comprises a bundle of fibers which in a known manner retains the unchanged distribution of radiation having passed therethrough but, in addition to this, it is desirable to employ some other optical components for deflecting the radiation or for eliminating possible inhomogeneities, it will be necessary to use components external of the bundle of fibers. These external components and the distance required thereby again result in lengths or sections which are exposed to the external atmosphere and, hence, to eventual faulty absorption.

As for the above-mentioned faulty absorption, the following more detailed comments can be made. Firstly, a measuring error caused by faulty absorption is the larger the stronger is the absorption occurring in the free sections of a radiation path, i.e. within sections free or open to the ambient atmosphere, in relation to the absorption occurring in a gas mixture contained in the sample chamber. Such faulty absorption occurs e.g. whenever the free or open sections of a radiation path are subjected to disturbance gases which absorb radiation on the measuring wavelengths of an analyzer. According to the Lambert-Beer law, the strength of faulty absorption depends on the concentration of a disturbance gas and the length of the open sections of a radiation path. Fluctuation in the concentration of disturbance gases produces a varying-size, unknown measuring error, which therefore cannot be simply compensated for. In addition, the size or magnitude of an error depends not only on the concentration of a disturbance gas component but also on the temperature and pressure of disturbance gases, even if other participating factors should remain unchanged. As an example, it may be noted that carbon dioxide and water vapour contained in air can in many instances lead to significant measuring errors. On the basis of prior known technology, the effect of faulty absorption occurring over the exposed sections of a radiation path can be reduced by any of the following means. First of all, the analyzer can be provided with two-ray optics, wherein the infrared radiation is guided to a detector alternately through a sample chamber and a reference gas chamber and wherein the concentration is measured on the basis of the relationship between sample and reference signals. This type of structure is disclosed e.g. in the above-cited publication HEWLETT-PACKARD JOURNAL, September 1981. However, this necessitates the use of moving mechanical parts, which increases the size and price of an analyzer and decreases its reliability. Also, the sensor itself becomes bulky and sensitive to vibration and other outside influences. A second option is to remove the infrared-radiation absorbing disturbance gases from inside the analyzer and to seal the entire apparatus hermetically. This is practically inconvenient, restricts the number of mechanical structural alternatives for an analyzer, and increases its price. Furthermore, as pointed out above in terms of minor components, the hermetic sealing is problematic and, thus, the sealing of an entire analyzer is not generally possible. A third option is that the analyzer be sealed almost hermetically and disturbance-gases binding materials be introduced therein. Even such near-hermetic sealing is inconvenient to implement and increases the price of an analyzer. In order to afford a suficiently long service life for the disturbance-gases binding materials, such materials must be allocated a major space within the analyzer, which leads to a large-sized analyzer and, moreover, the operator must take care of the fixed-term replacements of these materials. A fourth option is to reduce the length of the free sections of a radiation path in the direction of a measuring beam with respect to the length of a sample chamber. However, this will restrict the structural alternatives of an analyzer and e.g. the number of gases that can be analyzed. In many cases, the number of gases to be analyzed is in practice limited to one and, in theory, perhaps to two, unless the efforts of developing electronic components lead to future radiation sources and detectors that are considerably smaller than before. A fifth option is to introduce into the interior of an analyzer a protective gas not containing disturbance gases. However, this requires a protective-gas supply assembly and possibly also a replaceable protective-gas container and, thus, the apparatus will become very bulky and inconvenient to use.

The distribution of radiation to a number of detectors can be effected in a prior known fashion by using fiberoptics, as disclosed in the publication U.S. Pat. No. 5,254,858, whereby a section of the free length of a radiation path may be composed of these optical fibers. Nevertheless, even this embodiment requires, at least between a sample chamber and fiberoptics, a concentrator or the like component and possibly a respective light guide between a radiation source and the sample chamber in order to produce as homogeneous a radiation distribution as possible. A similar distribution of radiation to a variety of detectors is implemented in patent FI-95322 by using a branched wave tube structure. In both these cases, however, the path of radiation used for measuring develops substantial free sections exposed to disturbance gases, especially concentrators in the former publication and especially wave tubes in the latter publication.

BRIEF SUMMARY OF THE INVENTION

A principal object of the invention is hence to provide such an additional feature which is applicable for use in optical measuring sensors for the spectroscopic analysis of mediums, when the distance between a sample chamber containing a gas mixture to be measured and a radiation source and/or the distance between the sample chamber and a detector can both or either one be as long as otherwise necessitated by the measuring system and yet to avoid as thoroughly as possible the above-described faulty absorption caused by disturbance gases. A second object of the invention is to provide the above type of additional feature which thus enables a desired optical treatment of radiation arriving in and/or emerging from the sample chamber, such as the directing or distributing or equalizing thereof without optical restrictions and to a given desired number of detectors. A third object of the invention is this type of additional feature which does not, at any part of the apparatus, require gas-proof structures over the path of measuring radiation except of course at a possible sample chamber. A fourth object of the invention is that the absorption length of a measurement and the cross-sectional area of radiation through a gas mixture to be examined could be selected as much as possible to be suitable for a given purpose. Thus, it should be possible to select the absorption length in view of a gas component to be measured and the occurring concentrations thereof and the cross-sectional area so as to avoid errors caused by tainting etc. as well as to enable, if necessary, the measuring of several gas components also non-dispersively.

The above drawbacks can be eliminated and the above-defined objects are accomplished by means of the additional feature of the invention and by the method of the invention for constructing such an additional feature.

A benefit of the invention is that, by using an additional feature brought forth thereby, it is possible to implement an analyzer without moving parts while the effect of disturbance gases possibly contained in the ambient atmosphere or the like on the measuring result can be eliminated either completely or at least to such a degree that it bears no significance as far as measuring results are concerned. A second benefit of the invention is that this result is achieved while, at the same time, the lengths of a radiation path from a sample chamber to a radiation source and respectively to a detector or detectors can be as long as otherwise required by the measuring system and at the same time the measuring beam can have a cross-sectional area at the sample chamber as large as otherwise required by the measuring system. Indeed, it is often beneficial to provide the measuring beam with a cross-sectional area, having a diameter which is more than about 5 mm or even more than about 10 mm. Thus, it is possible to arrange either non-dispersively as many filter-detector pairs as necessary or, alternatively, to provide a dispersive arrangement and, hence, if necessary, it is possible to measure one, two, or a plurality of gas components reliably and in an optimal fashion, even if the ambient atmosphere should contain all these as disturbance components. A fourth benefit of the invention is that the analyzer itself or any part thereof, with the exception of the actual sample chamber, of course, need not be sealed gas tightly and there is no need to employ any containers or equipment relating to protective gases. A fifth advantage of the invention is that the absorption length of a sample chamber can be selected to be optimal in view of any given measurement. A sixth benefit of the invention is that, if desirable, the characterizing aspects of an additional feature brought forth thereby can be used for the guidance and/or alignment and/or distribution of light as desired and to so eliminate the need for possible other additional components in a measuring sensor. A seventh advantage of the invention is that, by using an additional feature brought forth thereby, the effect of said disturbance gases especially over the infrared range of an electromagnetic spectrum can be eliminated, even if the measuring should involve just one gas component or even several gas components over very narrow wavelength bands or wider wavelength bands.

BRIEF DESCRIPTION OF THE SEVERAL VIEWS OF THE DRAWING

The invention will now be described in detail with reference made to the accompanying drawings.

DETAILED DESCRIPTION OF THE INVENTION

FIGS. 1–5 depict several measuring sensor structures used for the spectroscopic analysis of mediums and especially gas mixtures and provided with an additional feature according to the invention. First of all, the measuring sensor generally comprises a per se known sample chamber 2 for a gas mixture to be analyzed, said sample chamber being provided with flow connections 5 and 6 for circulating the gas mixture to be examined through the sample chamber. In this case, the gas mixture to be analyzed is drawn to the flow connections either from the environment or from a gas-mixture containing pipe or from a tank containing the same. This type of sample chamber embodiments are illustrated in FIGS. 1–5 and 7. Alternatively, the flow connections and the walls of a sample chamber can be omitted for creating an environmentally open sample space 2, as depicted in FIG. 8. In this case, at least the sample space 2, which can also be regarded as a sample chamber, be it one without walls, must be included in a space from which the concentrations of a gas-mixture component or components are measured. Thus, the motion of a gas mixture taking place in said space, be it slight or vigorous, provides in itself a sufficient turnover in the sample chamber or respectively the sample space. The environments, in which the above-type of sample space 2 can be accommodated, may include outdoors e.g. for monitoring city air, indoors for detecting hazardous or harmful components, a gas container or flow duct for detecting changes in a gas mixture contained therein etc. The sample chamber and sample space are provided with at least two windows 3a and 3b transmissive to the applied radiation, the inner surfaces of said windows defining an absorption length L1 for measuring. Thus, the windows 3a and 3b of the sample chamber 2 have inner surfaces 13a and 13b (see FIG. 5) for holding therebetween a gas mixture to be analyzed, and the absorption of radiation from a gas component to be measured, which absorption is used for producing a measuring result by means of a detector 9, only occurs in a subsequently described system or arrangement of the invention over this absorption length L1. In the illustrated embodiments, the windows 3a and 3b are parallel and opposite to each other but may also be set at an angle relative to each other in a fashion not shown in the figures, whereby the measuring beam reflects from the opposite, appropriately designed wall of the sample chamber. Other designs for the sample chamber 2 are also conceivable but, in any case, it includes two radiation transmitting windows, one for introducing the measuring radiation into the sample chamber and the other for delivering the radiation from the sample chamber. The embodiment of FIG. 8 is also provided with windows 3a and 3b, the window 3a closer to a radiation source comprising an element made of a physical material as described above, such as a section of the hermetic jacket of a radiation source, but the window 3b closer to a detector being a so-called virtual window. This virtual window 3b comprises an entrance for a subsequently positioned light guide 4e, i.e. an aperture at a light guide end 15 closer to the access side of radiation, and includes in this case no element of physical material. However, the absorption length L1 can be considered to terminate in this interface, i.e. the second window without material, since the light guide is provided with a distinct inlet aperture, and within the light guide 4e the advancing characteristics of radiation R differ from those over the absorption length. It is obvious that the window 3a closer to a radiation source may also and respectively be the above type of virtual window, whenever the question is about an open radiation source. In this case, the open emitting surface of a radiation source provides this virtual window 3a. This type of sample chamber design enables the selection of a suitable absorption length L1 at a given time and the use of a suitable window size, whereby the sample chamber can thus be optimized for the type, concentration, and number of gases to be measured.

Figure 1:
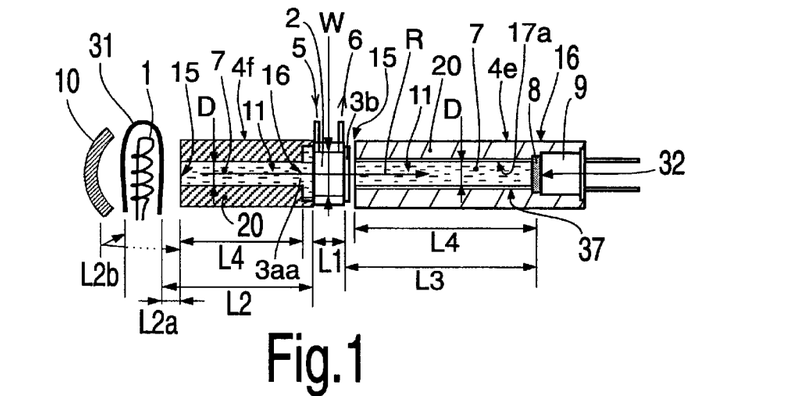
FIG. 1 shows a first embodiment for a non-dispersive measuring sensor including an additional feature of the invention for measuring the concentration of a single gas component in a longitudinal section in the radiation advancing direction.
Figure 2:
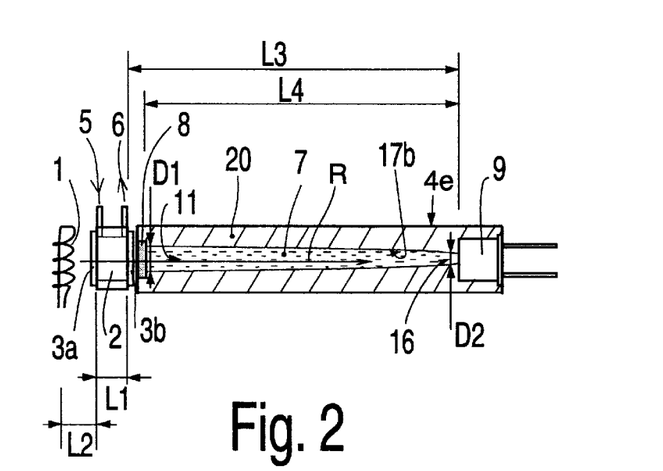
FIG. 2 shows a second embodiment for a non-dispersive measuring sensor including an additional feature of the invention for measuring the concentration of a single gas component in a view identical to FIG. 1.
Figure 3:
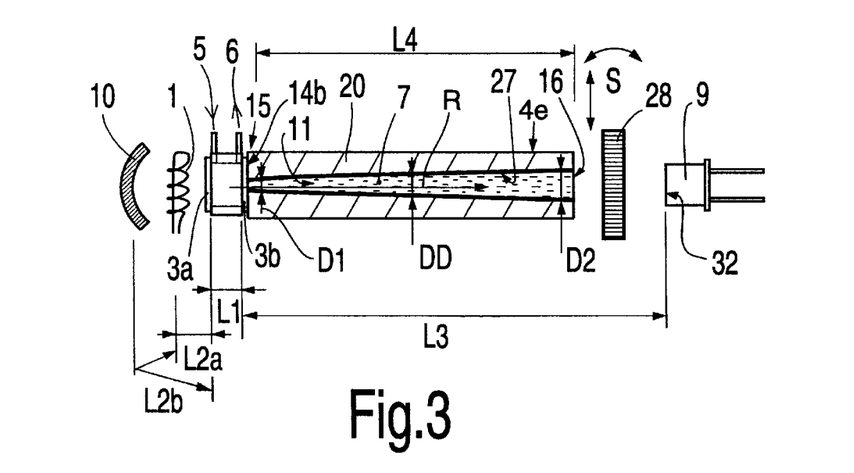
FIG. 3 shows a third embodiment for a non-dispersive measuring sensor including an additional feature of the invention for measuring the concentrations of given desired gas components in a view identical to FIGS. 1–2.
Figure 4:
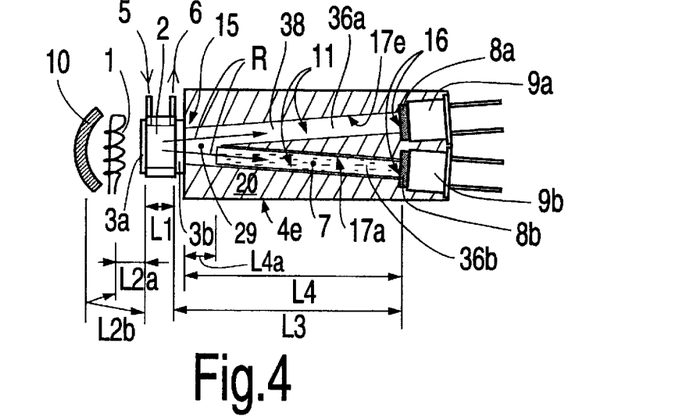
FIG. 4 shows a fourth embodiment for a non-dispersive measuring sensor including an additional feature of the invention for measuring the concentration of two gas components in a view identical to FIGS. 1–3.
Figure 5:
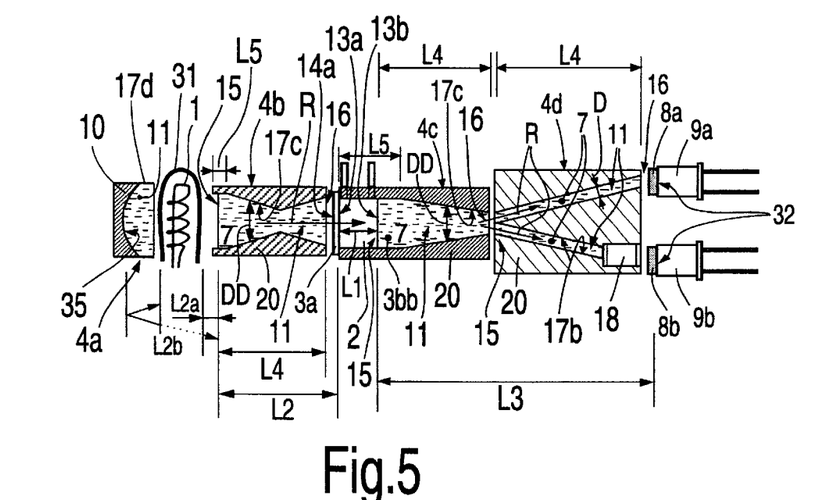
FIG. 5 shows a different type of fifth embodiment for a non-dispersive measuring sensor including an additional feature of the invention for measuring two gas components in a view identical to FIGS. 1–4.

The measuring sensor includes a radiation source 1, the radiation emitted thereby hence progressing through a first window 3a, an absorption length L1 in a sample chamber 2, and further through a second window 3b. Normally, the radiation source 1 comprises a prior known or some novel structure emitting infrared radiation over a wide or narrower wavelength range. In addition, the measuring sensor includes one or a plurality of detectors 9, 9a, 9b, which is or are optically directed towards this second window, i.e. directly towards the window, as shown in the figures, or by way of mirrors or lenses, which is readily conceivable. Between the radiation source 1 and each detector 9 lies either an optical filter 8 or filters 8a, 8b, which is or are permeable to a certain wavelength band, i.e. the absorption band of any given gas or gas component to be measured. In practice, the filters 8, 8a–8b are interference filters capable of establishing an exact definition for the absorption band and hence for the measuring band, when the plane of these optical bandpass filters is substantially perpendicular to a main radiation advancing direction R. This results in a non-dispersive measuring sensor, including either a single filter-detector pair, as shown in FIGS. 1 and 2, or a number of filter-detector pairs, as shown in FIGS. 4 and 5. It is obvious that, if necessary, it is also possible that the number of employed filter-detector pairs is more than the illustrated two, e.g. three or four, for detecting the desired gas components and determining the concentration thereof. It is also possible to employ an implement 28, such a grid or lattice (see FIG. 3), producing the dispersion of radiation, which is manipulated or inclined in a per se known manner according to a grid type relative to the main radiating direction R in a direction S for supplying the detector 9 with the spectral distribution of radiation from a greater or wider range. It is also possible to maintain the grid or the like stationary and to manipulate the detector 9 relative thereto. The implement 28 producing the dispersion of radiation may be placed not only between the sample chamber 2 and the detector 9, as shown in FIG. 3, also between the sample chamber 2 and the radiation source 1, which is not shown in the figure. Furthermore, in the case of FIG. 2, wherein the measuring is effected over a single wavelength band only, the optical bandpass filter 8 is placed between the radiation source 1 and the sample chamber 2. In the case of FIG. 1 it is also possible to apply this filter position depicted in FIG. 2.

In most practical cases, between the inner surface 13a of the first sample chamber window 3a and the radiation source 1 there is a first distance or length L2 and/or L2a and/or L2b and between the inner surface 13b of the second window 3b and the detector 9 or a number of detectors there is a second length L3, said lengths or distances totalling at least about 20% of said absorption length L1 of the sample chamber. If the radiation source is not provided with a hood, said lengths are measured from a filament or the like included in the source. If the radiation source is hermetically sealed within a hood 31, like an ordinary bulb, said lengths are measured from the closest mean surface of the hood 31, i.e. from the surface closest to the sample chamber, and by way of a mirror 10 from the surface facing away from the sample chamber, the distance between the opposite sides of the hood being ignored over the return path, as shown in the figures in reference to the lengths L2a and L2b. Of course, the radiation source 1 may be of the type provided with no mirror, whereby the section L2b does not exist. The invention offers advantages which are the more significant, the longer the first length L2 and/or second length L3 are with respect to said sample chamber absorption length L1. Thus, the invention is particularly preferable in measuring sensors, which are provided with light guides 4a–4f shown in FIGS. 1–5 and especially with actual wave tubes 4d, 4e, and 4f depicted in FIGS. 1–5.

It is particularly appropriate to employ a solid material 7 of the invention in such measuring sensors, in which at least one of the first length L2 between the inner surface 13a of the first window and the radiation source and/or the second length L3 between the inner surface 13b of the second window and the detector 9 or, respectively, detectors 9a–9b is at least about 40% of said absorption length L1. In most practical applications, the use of a solid material of the invention is warranted or at least offers a significant benefit, if at least one of these lengths, either the first length L2 or the second length L3, is at least approximately 1,5 times relative to said absorption length L1. In practice, the use of solid material 7 of the invention is unavoidable if at least one of these two lengths, either the first length L2 and/or the second length L3, is approximately five-fold or more relative to said absorption length L1. The above values apply whenever the ambient atmosphere is roughly conventional, such that people are exposed to in their normal living environment and especially in a hospital operating theatre. If the measuring sensor is used in facilities and environment, wherein exceptionally high concentration values of disturbance gases are possible, i.e. high concentration values of such gases which may affect detection of the presence of a gas component to be examined and its concentration measuring result, e.g. plenty of carbon dioxide or water vapour or some other adverse gas component, the use of a solid material of the invention is important and has a major significance even at quite low values of the first length L2 and/or the second length L3.

Figure 11:
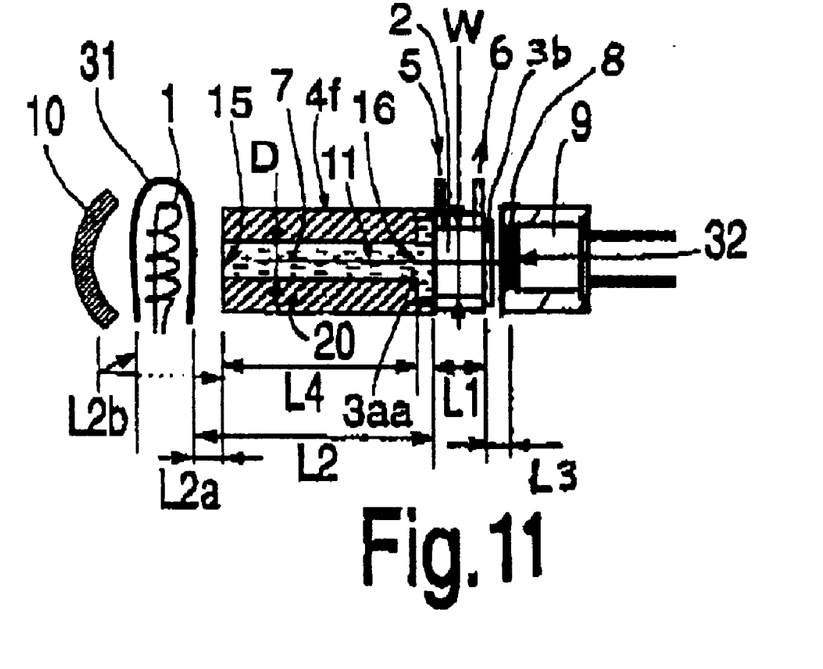
FIG. 11 shows another embodiment of the measuring sensor.

According to the invention, the first length L2 between the inner surface 13a of the first sample chamber window and the radiation source 1, and its possible sub-sections L2a and/or L2b, consists of a solid material 7 permeable to the applied radiation wavelengths, said material covering substantially all other sections of the radiation path except those facing possible gas filters, actuators and/or the like. See for example, FIG. 11. Likewise, according to the invention, the second length L3 between the inner surface 13b of the second sample chamber window 3b and the detector 8 or detectors 8a–8b consists of a solid material 7 permeable to the applied radiation wavelengths, said material covering substantially all other sections of the radiation path except those facing possible gas filters 18, actuators, such as a grid, a prism, or some other dispersion-producing element 28, a possibly open beam distribution section 29 in a wave tube combination and/or the like. Furthermore, according to the invention, this solid material 7 permeable to the applied radiation wavelengths is as homogeneous as possible at least in the direction transverse to the main radiating direction R. It should be noted that, in case the radiation source is hermetically enclosed in the hood 31, as depicted in FIGS. 1 and 5, the first length L2 and the second length L3 are of course filled with said solid material 7 over those sections which lie outside the hood 31 of the radiation source 1. In other words, the distance between the surfaces of the hood 31 of the radiation source 1 opposite to each other in the radiation direction R need not be taken into consideration. Likewise, if the detector 8, 8a–8b etc. is enclosed hermetically, which is usually the case, it is not necessary to worry about the distance between a detector window 32 and the radiation sensitive surface, but the second length L3 can be measured to the detector window 32. In case the radiation source 1 is hoodless, as in FIGS. 2 and 3, the second length L2 must be considered to be first of all the distance L2a between the emitting surface or filament of the radiation source 1 and the inner surface 13a of the first sample chamber window, and in addition, if there is a mirror 10 behind the radiation source 1, it is necessary to consider the distance covered by the radiation thereover to the inner surface of the first window, i.e. the distance L2b, as indicated in FIG. 3. Corresponding distances or lengths develop also in connection with a hooded radiation source and a mirror 10, as in FIG. 5, whereby the only distance ignored is that between the opposite surfaces of said hood, as explained above. In the subsequent description, however, the designation first length L2 is also used to indicate the combined effect of these two sub-lengths L2a and L2b described in the previous sentence as well as to indicate the lengths measured to the hood 31 from both an enclosed and open radiation source 1. Likewise, the subsequent description uses the term second length L3 to indicate all distances to the detector 9, no matter whether the path includes gas filters 18, actuators, such as grids 28 and/or beam distribution sections 29, mirrors not shown in the figures, as well as to the window 32 of an enclosed detector as to the photosensitive surface of a non-enclosed detector.

Since, according to the invention, the solid material 7 permeable to the applied wavelengths is as homogeneous as possible in the direction transverse to the main radiating direction R, the radiation can be manipulated with any given optical means exactly as if the first length L2 and the second length L3 consisted of some gas or vacuum, since such transversely homogeneous material 7 in itself does not guide the radiation in any given direction. Thus, the guidance of measuring radiation can be planned relatively freely as desired, the particularly noteworthy factor being of course a given refractive index of the solid material and its difference from the refractive indices of other optical components. However, this only requires that the design of optical components be calculated according to the difference between the refractive indices, e.g. with otherwise known means. The solid material 7 of the invention may first of all comprise either the material of the first sample chamber window, as in FIG. 1, wherein said material makes up this first window 3aa and extends, preferably as a single element, from the inner surface 13a of said window towards the radiation source 1 and typically as close to it as possible. The result, on the side closer to the radiation source, is a very thick sample chamber window 3aa, having a thickness which in this case matches a length L4 for a subsequently described wave tube. Exactly the same way, said solid material 7 may comprise the material of the second sample chamber window, which preferably extends in a single element from the inner surface 13b of said second window towards the detector 9 or detectors 9a–9b for creating a very thick second window 3bb, as shown in FIG. 5. These thick windows 3aa and 3bb cover at least some essential section of either the first length L2 and/or the second length L3. In the case of FIG. 1, the first thick window 3aa extends substantially all the way to the radiation source 1 and covers the first length L2 almost entirely, while in the case of FIG. 5, the second thick window 3bb only covers a part, i.e. about a half of the second length L3. It is obvious that the thick first window and/or the thick second window may also cover any other section of either or both lengths L2 and/or L3. Another alternative is to employ, as said solid material 7, a separate element made of the sample chamber window material, having an appearance which is adapted to match any given required shape. This element is placed e.g. between an outer surface 14a of the first sample chamber window 3a and the radiation source, as in FIG. 5 between the mirror 10 and the radiation source 1, for covering or filling the section L2b of the first length. Similarly, it is possible to employ the same material as the sample chamber window material and to place it in a suitable shape and a suitable size between an outer surface 14b of the second sample chamber window 3b and the detector 9 or detectors 9a–9b, whereby it fills a substantial section of said second length L3. This type of solution is depicted e.g. in FIG. 1, wherein between the sample chamber 2 and the filter-detector assembly 8, 9 is fitted a cylindrical element of the material of the invention as a light guide 4e inside a housing 20, said element having a length which constitutes e.g. a wave tube length L4, as well as in FIG. 4, wherein one of the branch sections, i.e. a branch 36b extending to a filter-detector assembly 8b, 9b, of a light guide 4e downstream of the beam distribution section 29 following the sample chamber 2 in the radiating direction, said branches in this case comprising subsequently described wave tubes, is filled with a solid material 7 the same way as shown in FIG. 1. In the latter case, just part of the length L4 of the light guide 4e, and concerning just one of its branches, is filled or covered with the material of the invention.

The solid material 7 of the invention may also comprise some other solid material permeable to the applied radiation wavelengths and having an outline which matches any given shape and size, said material being placed between the outer surface 14a of the first window of the sample chamber 2 and the radiation source 1 or, respectively, between the outer surface 14b of the second window 3b and the detector 9 or detectors 9a–9b. In this solution, the solid material 7 may be in direct contact with either or both windows, as with the window 3b in FIG. 3, or there could be a gap between the same and the window or windows, as shown with the window 3b in FIGS. 2 and 4. However, the most preferable solution is to design all gaps, into which the ambient atmosphere could be able to penetrate in the radiating direction R, as small as possible throughout the length of a radiation path. Thus, the first length L2 between the inner surface 13a of the first window 3a of the sample chamber 2 and the radiation source 1 or, in an alternative case, the hermetically sealing radiation source shroud 31 is filled as compactly as possible with said solid material 7 permeable to the applied radiation wavelengths. Likewise, the second length L3 between the inner surface 13b of the second sample chamber window 3a and the detector 9 or, respectively, detectors 9a–9b or, in an alternative case, a shroud 32 hermetically sealing said detector is filled as compactly as possible with said solid material 7 permeable to the applied radiation wavelengths. This is an appropriate objective to pursue and it is possible to apply any means described in the previous paragraphs, i.e. by providing the sample chamber with such a thick first window or second window or both windows or by using the sample chamber window material or some other subsequently described material to construct structural components, which are placed between the outer surfaces 14a and 14b of the sample chamber windows 3a, 3b and the radiation source 1 and, respectively, the detector 9, as described above. Here, it should be noted, however, that if the concentration of a disturbing gas component in the ambient atmosphere is relatively low with respect to the concentration of the same gas component in a gas mixture to be analyzed, which is the case e.g. with carbon dioxide when measuring the gas components of a patient's alveolar air, it is in most cases sufficient that just some section of the first and/or second length L2, L3, and particularly that section of a radiation path in which the radiation representative of this component passes, be filled with the solid material 7 of the invention. In the construction shown in FIG. 4, the filter-detector pair 8a, 9a measures a gas component which is not present in the environment and, thus, this branch 36a of the light guide 4e can be open without any hazard of faulty absorption that would distort the measuring result. Thus, in the above-mentioned branch, the filter-detector pair 8a, 9a operates over a wavelength range in which no substantial absorption occurs as a result of a gas mixture 38 contained in the wave tube. On the other hand, the filter-detector pair 8b, 9b measures such gas component which is present to some degree, but not in very high concentrations in the environment. In this case, the other branch 36b of the light guide 4e is filled with the solid material 7 for minimizing errors appearing in the signal of the detector 9b. In the wave tube 4e, the beam distribution section 29 has a length of L4a, and hence a volume, which is so short compared to the second length L3 and the overall wave tube length L4 that a disturbance gas contained therein does not yet have an adverse impact on a signal produced by the detector 9b. Typically, the beam distribution section 29 has a length L4a which constitutes no more than about 30% of the length L4 of an entire light guide, such as a wave tube, and thus usually also of the second length L3. Preferably, the length L4a has a share of the length L4 and the second distance L3 which is no more than 25% and typically 10–20%, for example about 15%. In the case of FIG. 4, however, the beam distribution section 29 could just as well be entirely filled with the solid material 7, whereby essentially the entire radiation path throughout the wave tube length L4 to the detector 9b will be protected from outside disturbance factors. Even in this case, the wave tube branch extending to the detector 9a can be left open. That end surface of an element filling the beam distribution section 29, which faces towards the detectors, should appropriately be either a plane parallel to the second window 3b or a cylindrical surface or a spherical surface or a polyhedron, wherein the surface sections aligned with the wave tube branches are perpendicular to the medial line of a given branch. In the case of FIG. 5, in turn, the light guide, such as a wave tube 4d, has both branches, one extending to the filter-detector pair 8a, 9a and the other to the filter-detector pair 8b, 9b, filled with the solid material 7 of the invention with the exception of the gas filter 18. In the case of FIG. 5, the beam distribution section develops over the area of an outlet end 16 of the concentrator 4c and an inlet end 15 of the wave tube assembly 4d and is therefore substantially filled with the solid material 7.

The solid material 7 of the invention should appropriately be made as homogeneous as possible also in the main radiating direction R as that is the simplest manner to calculate and establish control over the passage of radiation. Other surfaces of the solid material 7, excluding those permeable to the actual measuring beam, and including e.g. lateral surfaces 17a, 17b (in wave tube 4d), 17d, 17e parallel to the main radiating direction R or lateral surfaces 17b (in wave tube 4e) gently converging in the main radiating direction or lateral surfaces 27 gently diverging in the main radiating direction or lateral surfaces 17c sharply converging or diverging in the main radiating direction, can be treated in a variety of ways according to what is required. These lateral surfaces can be shiny, such as surfaces 17a, 17b, 17e and 27 in FIG. 5, for creating reflection for the measuring radiation passing through. This reflectivity can be created by providing the solid material 7 itself with a shiny surface, such as surfaces 17a in FIGS. 1 and 4, or this brightness or glossiness may be a result of the glossiness of the inner surface 17b and 17e of a surrounding sheath 20, as in FIGS. 2 and 4, or the solid material 7 may have its surface 27 coated with a glossy finish by some suitable means, e.g. by finishing the polished surface by vaporization or some other conventional or novel mirror finishing technique or by coating with an interference mirror finish. The solid material 7 of the invention can also be provided with diffusely radiation-reflecting surfaces 17c, as in concentrators 4b and 4c in FIG. 5, said surfaces being dull and, if necessary, coated with a suitable diffusely reflecting finish. This diffusely reflecting finish can be provided directly on the very surface of the solid material 7 or by means of the inner surface of the sheath 20 surrounding the same. It is also possible to make these surfaces of the solid material as little reflecting as possible, e.g. by making the same dull and by blackening, such as the lateral surface 17d of a light guide 4a associated with a mirror 10 in FIG. 5. According to its design, a single measuring sensor can be subjected to one or more of these finishing methods as for the solid material 7 of the invention, depending on the propagation characteristics of measuring radiation set for a particular area. It is obvious that any given element of the material 7 permeable to the applied wavelengths and the respective wave tube sheath 20 are provided with radiation-transmitting ends 15 and 16. Generally, these ends are bright and either straight or designed as a lens surface. Also, the wave tubes not provided with a material of the invention, such as the branch extending to the filter-detector pair 8a, 9a in FIG. 4, are provided with similar, but generally open ends 15, 16.

The solid material 7 of the invention may comprise any material permeable to the applied wavelength, whether it be some amorphous solid and compact material, such as e.g. infrared-radiation transmissive glass or other silicate. The solid material of the invention may also comprise some crystalline material permeable or transmissive to the applied wavelengths, such as a salt of some metal, e.g. calcium fluoride or fluoride of some other metal. Thus, such solid material 7 transmissive to the applied radiation wavelengths may usefully consist of a compound of some suitable metal, i.e. generally the salt of a metal, such as arsenide, fluoride, bromide, chloride, iodide, selenide, telluride or sulphide or a mixture thereof or a combination salt thereof. The combination salt refers to a compound of any of the above non-metals with two different metals or, respectively, a compound of one metal with several above non-metals, such as tallium-bromide-chloride. The compound may also comprise oxides of various metals, oxide combinations, silicon or germanium, either in a monocrystalline or polycrystalline form, such as e.g. aluminium oxide or sapphire in a substantially colourless form, and previously mentioned suitable silicate, such as glass or quartz in an appropriate form. These materials can also be compounded with some suitable additive or additives either intentionally or those can be present as an impurity. These various compounds or pure materials or mixtures can be used in per se known manners for producing solid elements with several different methods. First of all, an element can be produced by using the molten phase of a material, resulting either in an amorphous or crystalline solid material, and the desired element can be designed after the melt has congealed to a solid state. If the measuring sensor is provided with the sheath 20 of a suitable material, the melt can be cast directly into this light guide, if that is desirable. Another possibility is to start with one of these above-mentioned materials in a pulverized or powdered form and to press it to a desired final shape, the result being usually a crystalline solid material. For example, potassium bromide can be readily pressed to a desired form. In this case, as well, the pressing can be effected either in a separate device and the finished element transferred to an assigned measuring sensor or, if the measuring sensor includes a sheath 20 of a suitable material, the pulverized material or powder can be pressed directly into a light guide to be included in this measuring sensor. In this case, the sheath 20 preferably includes a cylindrical straight length L5 e.g. in the main radiating direction R, as shown in FIG. 5 in reference to light guides 4b and 4c. This straight cylindrical section or length L5, which is preferably circular in its cross-section, enables the use of a material compressing piston directly into an internal space 11 of the sheath or housing 20 without having to employ separate moulds. In FIG. 5, the cylindrical section L5 of the light guide 4c has such a length that, after the compression of solid material 7, a part of the cylindrical section L5 constitutes the sample chamber 2 and its absorption length L1. Thus, in this case, into the internal space 11 within the sheath 20 of the light guide 4c is first pressed the solid material 7, which at the same time constitutes the second window 3bb for the measuring chamber 2 while the remaining portion constitutes the measuring chamber absorption length L1, which is followed by attaching the first window 3a of the measuring chamber 2 to the sheath 20. In addition, when applying the pressing technique, it is possible to effect a sintering process after the pressing or the pressed element can be used as such.

In addition to the above, the element of solid material 7 can be precipitated from a gas phase or solution by some suitable known method, the result being usually a crystalline material. Especially in this case, but also in all above cases dealing with manufacturing technique, i.e. through a molten phase or by pressing from powder, it is possible to design or shape sizable solid material elements outside the measuring sensor and to work these mechanically for components of a desired size and shape to be used in various parts of the measuring sensor. If monocrystal elements are desired, depending on the material, those must be made by precipitating either from a gas phase or a vapour phase or from a melt by very slow cooling or by additionally using zone melting. It depends on the size and shape of a required element of solid material 7 as well as on the desired material itself which manufacturing technique is appropriate at a given time. In FIG. 1, for example, the material 7 of the totally reflecting wave tube 4e and, in FIG. 4, the material 7 of the corresponding wave tube branch are probably most preferably machine-finished outside the measuring sensor from a larger crystalline or amorphous element manufactured by any of the above-described suitable techniques since, in this case, the solid material 7 of the invention is provided with a certain free or clear reflective outer surface 17a and a certain clear outer dimension D even though the wave tube constitutes part of the internal space 11 of the sheath 20. In the cases of FIG. 2, wherein the solid material 7 of the invention has a complicated shape, it is probably approriate to apply either the pressing of powder or casting of melt directly into the internal space 11 of the sheath 20 since, in these cases, the wall surface of the sheath 20 is also a factor in determining the optical properties for the surface 17b. As for the light guides 4b and 4c of FIG. 5, the manufacturing technique based on the pressing of powder has already been discussed. However, there is nothing to prevent the solid material 7 of these light guides 4b, 4c from being manufactured just as well by casting of melt. As for the light guide 4a of FIG. 5 and the light guide 4e of FIG. 3, it is probably appropriate to manufacture those from an amorphous or crystalline material element, as these guide are provided with finishes 27 and 17d discussed previously in this specification. The light guide of FIG. 1, such as a wave tube 4f, can be manufactured by any of the described methods, and the same applies to the light guides of FIG. 5, such as wave tubes 4d.

In principle, it is further possible that the solid material 7 of the invention be comprised of a gel or an equivalent material combination, which due to its shape permanence can be regarded as a solid material, or some suitable plastics. The liquid and a gelling agent therefor can be cast directly inside the sheath 20. The plastics can either be machined from an existing solid block or it can be cast as a liquid inside the sheath 20 and allowed to set, i.e. polymerize, within the sheath into a solid material transmissive to the applied wavelengths.

The use of a solid material 7 of the invention transmissive to the applied wavelengths is especially preferable whenever the measuring sensor is provided with light guides 4b–4f, having a length L4 which is at least about one and a half times, preferably at least three times, and typically at least five times with respect to its mean diameter D or DD. If desired, this limitation applies to all described embodiments. The light guides are either provided with a sheath or housing 20 of a rigid material, as in FIGS. 2–4, or the rod constituting an actual light guide consists of a rigid material 7 of the invention, such as the light guide 4e in FIG. 1. The ones shown in the figures are this very type of light guides. In FIG. 1, between the radiation source 1 and the measuring chamber 2 lies a light guide 4f, which in terms of its length L4 is about quadruple relative to the diameter D, the latter remaining constant throughout the length of the light guide 4f. In FIG. 1, between the measuring chamber 2 and the filter 8 and the detector 9 lies a light guide 4e, having a length which is about quintuple relative to its diameter D, the latter also remaining constant throughout the length of the light guide 4e. As for this structure shown in FIG. 1, it should be noted, however, that the above definition of length applies to the length of a combination consisting of these two light guides, i.e. the light guides 4f and 4e must in this case have a total length which is at least about one and a half times, preferably at least triple, and typically at least quintuple relative to its mean diameter D or DD. FIG. 2 illustrates a light guide 4e, having a diameter D1 adjacent to the sample chamber 2 which is slightly longer than a diameter D2 at the end of the filter 8 and the detector 9. In this case as well, the mean diameter is substantially less than a fifth the entire light guide length L4. On the other hand, FIG. 3 illustrates a light guide 4e, having a diameter D1 adjacent the measuring chamber 2 which is shorter than a diameter D2 at the end closer to the dispersion producing implement 28 and the detector 9. However, even in this case, the mean diameter DD is substantially less than a fifth of the entire light guide length L4. FIG. 4 also illustrates light guides 4e between the measuring chamber 2 and a plurality of filter-detector pairs 8a and 9a, 8b and 9b. The operation of this light guide is otherwise similar to that of the light guide 4e of FIG. 1, except that, over the section 29, it distributes a part of the radiation passed through the sample chamber 2 to one filter-detector assembly and a part to another filter-detector assembly whereby, in one branch 36b, the reflective surface is primarily constituted by the outer surface 17 a of a solid material and, in the other branch 36a, by the inner surface 17e of the sheath 20. The light guides 4f and 4e and 4d, and especially the possible above-described branches thereof, fulfilling the above-defined dimensioning conditions are all so-called wave tubes which set the main direction R of radiation passed through the sample chamber 2 or entering the sample chamber 2 to be such that it falls on the filter 8, 8a–8b or on the dispersion producing implement 28 at an angle of incidence, which is less than +–10° relative to the bisector of the filter 8 and 8a and 8b. In other words, the wave tube 4d–4f produces a roughly parallel beam of rays, wherein the rays do not deviate or deflect by more than e.g. +–10° from the main propagating direction R, which is parallel to the longitudinal median line of the wave tube, the part of radiation emitted from the radiation source at another angle damping in the wave tube as a result of several reflections. This type of constructions are shown in FIGS. 1 and 3–5. Alternatively, it may also be possible to let a beam of scattered rays fall on the filter 8, whereby the filter also emits radiation passed therethrough at an incorrect angle but this faulty radiation is eliminated by means of a wave tube 4b set between the filter and the detector 9, as shown in FIG. 2. In the solution of FIG. 2, by virtue of the wave tube, the detector is only hit by that portion of the filter-penetrated radiation which has landed on the filter, as described above, at an angle of incidence less than +–10°, while the radiation fallen on the filter at a wider angle of incidence damps in the wave tube as a result of several reflections so as not to produce a result-affecting faulty signal in the detector. The described system or arrangement makes sure that a correct signal is obtained from the detector 9, 9a, 9b, since the filters 8, 8a, 8b are generally interference filters, whereby a substantial deviation in the radiation propagating direction should not occur or, at least, such substantially deviating radiation must not end up all the way in the detector in order to produce a reliable measuring result. The same applies also to the dispersion producing implement or device 28, which also produces unreliable results if it receives radiation from other than the planned direction.

As for the above, the internal space 11 of the light guide 4a–4f refers to a space defining the beam of applied radiation, whether it be constituted by an inner surface 37, 17b, 17c, 17e of the sheath 20 or by an outer surface 17a, 17b, 17c, 17d, 27 of the solid material 7 of the invention, or by a coating 27, 17d of the solid material 7. As can be noted, the inner surface of the sheath 20 and the outer surface of the solid material 7 can be a common interface and, likewise, the outer surface and coating of the solid material 7 can be a common interface. Thus, the wave tube 4e of FIG. 1 may be constituted by the inner sheath surface 37, if the outer surface 17a of the solid material 7 allows radiation therethrough both outwards and inwards. Alternatively, the wave tube 4e of FIG. 1 may be constituted by the outer solid material surface 17a, when the latter is either totally reflective or does not allow the radiation, which has found its way between the surfaces 17a and 37, back within the solid material. In the former case, the internal space 11 is only partly filled with the solid material 7, since there is a small gap from the outer surface 17a to the inner surface 37 of the sheath 20. Hence, the solid material of the invention, which is homogeneous in the direction transverse to the radiating direction, is allowed to pass radiation even through its outer surface parallel to the light guide or wave tube as long as the inner surface 37 of the radiation-impenetrable sheath 20 is a sufficiently small distance away. In this respect, the material of the invention may without any problems differ from optical fibers which are non-homogeneous in the direction transverse to the radiating direction, consisting of an optical core and an optical jacket. In constructions of the invention, a small gap between the surfaces 17a and 37 has no significance in terms of faulty absorption since, first of all, the gap is small, being no more than about 15% of the mean diameter of a light guide and preferably no more than 10% or 5% or less of this mean diameter D, DD, and since the radiation travels in this gap a very short distance relative to the length L4 of a light guide, and especially the wave tube 4d, 4e, 4f. The sheath 20 mentioned in this text may be so sturdy as to its wall thickness that it constitutes a load-bearing structure for the light guide, which is typically the case if the solid material is pressed of powder or cast as a melt into the sheath 20. However, the sheath 20 may also be very thin, being constituted e.g. by a mere coating of the solid material. Thus, in FIG. 5, the coating 17d can be regarded as a sheath and similarly in FIG. 3 the coating 27 could in itself constitute a sheath, provided that the solid material 7 of the wave tube 4e is of such a quality that it sustains itself and the forces applied thereto. Thus, the most essential feature of the sheath is that it is impermeable to the applied wavelengths, i.e. the sheath isolates the inner space 11 of a light guide from possibly disturbing external radiation. In addition to this basic quality, the sheath 20 can function as a mechanical shield, a fastener for the solid material 7 of the invention, and a load-bearing component.

FIG. 5 also illustrates light guides 4b and 4c, having a length L4 which is at least about 1,5 times over the mean diameter DD. In this case, however, the question is not about wave tubes which would provide a substantially parallel radiation but, instead, about per se known concentrators which direct homogeneous light into the sample chamber 2 and collect therefrom as homogeneous a radiation as possible to be carried forward. Furthermore, in FIG. 5, the gap between a reflective surface 35 of a mirror set behind the radiation source 1 and a hermetic shroud 31 of the radiation source is also filled with a material 7 according to the invention for creating a light guide 4a. The reason for filling this space 11 between a mirror 10 and the radiation source 1 is that the correct alignment of radiation requires that the mirror 10 be set at a certain distance from the radiation source and, thus, there exists a gap from which the ambient atmosphere must be eliminated. In addition to this, FIG. 5 illustrates a wave tube assembly 4d behind the concentrator 4c located in the radiating direction R downstream of the sample chamber 2, said assembly, in this case, consisting of two internal spaces 11, both of which are in this case filled with a radiation transmissive material 7 of the invention for also creating wave tubes as described above.

In all these cases, regardless of the type of material 7 transmissive to the applied wavelengths and regardless of its manufacturing technique, it is appropriate to press or cast or otherwise manufacture the material, no matter in which form it is used, so as to fill the first length L2 and/or second length L3 or a section thereof and, thus, particularly the internal spaces 11 of the light guides 4a–4f as non-porously as possible, i.e. to a filling degree as high as possible. Thus, the radiation path from the radiation source 1 to the sample chamber 2 and by way of light guides to the filter 8, 8a, 8b or to the dispersion producing device 28 and further to the detector 9 or detectors 9a, 9b, or some other type of, e.g. the above-described measuring radiation path, includes as few sections as possible which are exposed to ambient atmosphere. It should be appreciated that tiny gaps between various components do not have a significant disturbing effect. It should also be appreciated that the above-mentioned voidless filling of a radiation path with the solid material 7 must be proportioned to the accuracy of measurements to be made, to the concentration of a gas to be measured in a gas mixture to be analyzed and in a gas atmosphere surrounding the measuring sensor. Thus, certain exposed sections mentioned in the text may be included in a measuring sensor of the invention, while fulfilling the features of the invention.

Figure 7:
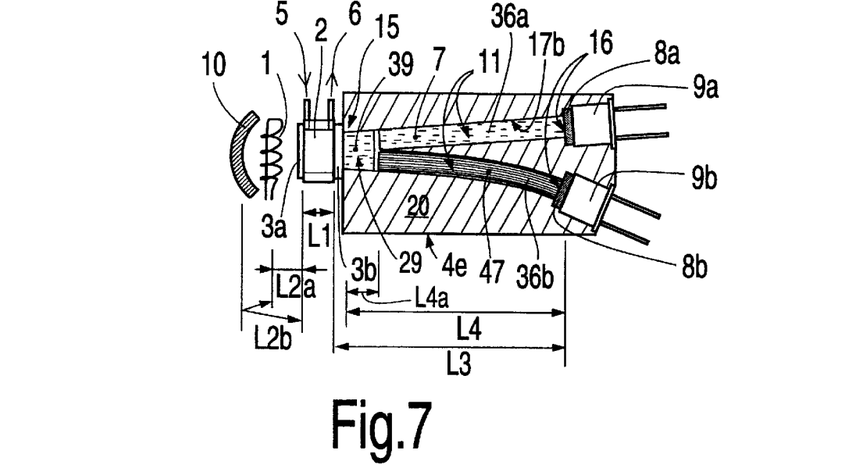
FIG. 7 shows a sixth embodiment for a non-dispersive measuring sensor including an additional feature of the invention for measuring the concentration of two gas components in a view identical to FIG. 4.
Figure 8:
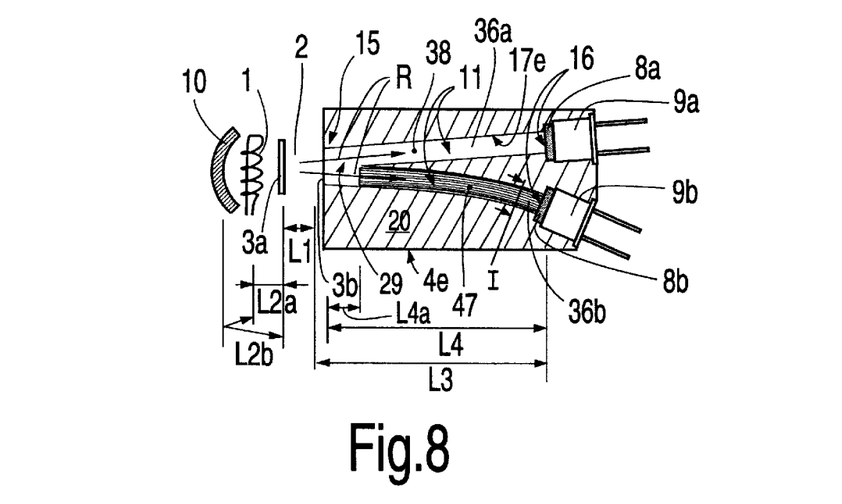
FIG. 8 shows a seventh embodiment for a non-dispersive measuring sensor including an additional feature of the invention for measuring the concentration of two gas components in a view identical to FIG. 4.
Figure 9:
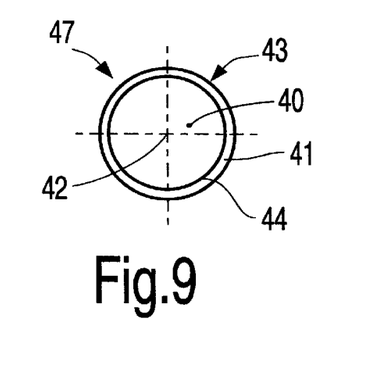
FIGS. 9 and 10 show cross-sections of non-homogeneous materials used in the embodiments of FIGS. 7 and 8 and filling one branch of a light guide.
Figure 10:
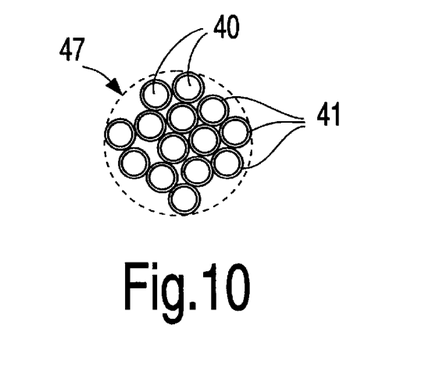

FIGS. 7 and 8 illustrate somewhat different embodiments. Here, the light guide 4e comprises, the same way as in FIG. 4, two branches 36a and 36b which extend from the surface or from the proximity of the surface of the second window 3b of the sample chamber 2 to the filter-detector pairs 8a and 9a, 8a and 9b. In these embodiments, the internal space 11 of one branch 36b is filled wither with a single, rather thick optical fiber 47, as shown in FIG. 9, or with a bundle of fibers 47 consisting of a number of optical fibers, as shown in FIG. 10. The optical fiber and the individual fibers included in a bundle of fibers consist in a per se known manner of a material constituting a core member 40 and of a surface layer surrounding the core member. Of course, the material of said core member 40 must consist of a substance transmissive to the applied wavelengths, having a refractive index which over the applied wavelength range exceeds that of the material of the surface layer 41, whereby the radiation advances within the core member of a fiber as a result of total reflection produced by an interface 44 between said core member and the surface layer. A corresponding total reflection also develops in a type of fiber, in which the refractive index diminishes in a stepwise or stepless fashion when progressing from a fiber centre 42 towards its outer surface 43, only in this case there is no distinctly detectable interface but, in a way, the interface spreads over a certain extent in the radial direction of a fiber. Thus, the optical fiber will be inevitably non-homogeneous in the direction transverse to the radiating direction. Such an optical fiber or a bundle of fibers prevents the access of an external gas atmosphere in between a detector and a sample chamber the same way as the above-discussed homogeneous solid material. However, as discussed above, the radiation that has passed through the fiber and and bundle of fibers 47 has optical properties which are different from those of the radiation that has traveled through the solid material 7, whereby it is possibly necessary to employ other types of elements guiding the passage of radiation. It is also obvious that various types of sensors or various sections of a sensor may set different quality requirements for the passage of radiation and, therefore, the solution employing fibers may be more preferred for a certain device or a certain section of a device while the homogeneous material is more preferred in some other section of a device. In the embodiment of FIG. 7, the internal space 11 of one branch 36a is filled with the above-described solid material 7 for producing a wave tube, as described earlier in the text. On the other hand, in the case of FIG. 8 the internal space of the branch 36a is filled with a gas mixture 38 originating from ambient gas atmosphere, i.e. it is filled with air, for also producing a wave tube, as described earlier in the text. Indeed, this solution is applicable whenever the filter-detector pair 8a, 9a is used for measuring a gas component not present in the environment in a disturbing amount. Contrary to wave tubes, in the case of optical fibers and bundles of fibers, the ratio between the diameter and length thereof has no significance in terms of the alignment of radiation, provided that the fibers exceed a certain minimum length.

The radiation emerging from the measuring chamber 2 by way of the second window 3b is distributed for two or more filter-detector pairs over a beam distribution section 29, whose principle has already been discussed. In FIG. 7, the beam distribution section comprises a material element 39, preferably consisting of one of the above-mentioned solid materials 7 of the invention. In FIG. 8, the beam distribution section comprises an air-filled void. In the case of FIG. 7, the second window 3b can of course be arranged to comprise a material element 39 constituting the beam distributing section 29.

An additional feature of the invention, i.e. arranging a solid material over a section which covers as much as possible of the length of a measuring radiation path, is particularly preferred when the measuring is effected over the infrared range of radiation, which is typical when measuring alveolar air in various occasions. In this case, after all, at least carbon dioxide is a common and easily harmful disturbance gas, but also other various gas components, such as those occurring in anesthesia and alcohol concentration measurement, may be present as disturbance gases whose possible effect must be eliminated. Above, this specification has described e.g. solid materials suitable for the infrared range. However, there is nothing to prevent the use of an additional feature of the invention also over a visible wavelength range or an ultraviolet range, as long as a solid material of the invention is selected to be transmissive to the applied wavelength band or wavelength bands.

We claim:

1. A measuring sensor for subjecting one or more gaseous components in the breathing gases of a subject to analysis by infrared radiation absorption, a gaseous component analyzable by infrared radiation absorption also being present in ambient air, said measuring sensor comprising:

a radiation source (1) for emitting infrared radiation along at least one radiation path (R) in the sensor;

a sample volume (2) for containing a sample of the breathing gases to be analyzed, said sample volume having a pair of spaced ends defining a measuring absorption length (L1) therebetween, said sample volume being interposed in the radiation path of said sensor so that radiation is applied to a first end, passes through the breathing gas sample in said sample volume along the measuring absorption length, and exits the sample volume through a second end, said radiation source being spaced from said first end of said sample volume, along the radiation path, by a first length (L2);

a least one detector (9, 9a, 9b) in the radiation path downstream of said sample volume, said at least one detector being spaced from said second end of said sample volume, along said radiation path, by a second length (L3), the sum of said first and second lengths being at least substantially 20% of said measuring absorption length (L1) of said sample volume;

means (8, 8a, 8b, 28) interposed in said radiation path between said radiation source and said detector for establishing a desired wavelength band of infrared radiation; and a solid material transmissive to infrared radiation and substantially homogenous transverse to said radiation path (R), said solid material having a desired rigid and fixed shape and being positioned along the radiation path (R) in at least one of the first and second lengths (L2, L3) of said radiation path to displace ambient air from the radiation path (R) and avoid undesired inaccuracies in the analysis of the breathing gases.

2. A measuring sensor as set forth in claim 1 wherein said sensor has a single radiation path in the sensor.

3. A measuring sensor as set forth in claim 1 wherein said measuring sensor has a plurality of radiation paths, in each of which a detector is positioned downstream of said sample volume, each of said radiation paths having means for establishing a desired infrared radiation wavelength band interposed therein, said solid material being positioned along at least one of said radiation paths in said second length (L3) of said radiation path.

4. The measuring sensor as set forth in claim 3 wherein said second length of one of said radiation paths contains said solid material and the second length of another of said radiation paths contains ambient air.

5. The measuring sensor as set forth in claim in claim 3 wherein said second lengths of at least two of said radiation paths contain said solid material.

6. The measuring sensor as set forth in claim 3 wherein said solid material is positioned along the second length of one of said radiation paths and wherein another of said radiation paths is occupied, in said second length, by one of a solid material transmissive to infrared radiation and substantially homogenous transverse to said another radiation path or by an optical fiber means transmissive to infrared radiation.

7. The measuring sensor as set forth in claim 1 wherein said solid material is positioned in said first length (L2).

8. The measuring sensor as set forth in claim 1 wherein said solid material is positioned in said second length (L3).

9. The measuring sensor as set forth in claim 7 wherein said solid material is positioned in both said first and second lengths (L2, L3).

10. The measuring sensor as set forth in claim 1 wherein said sample volume has a window at at least one of said ends.

11. The measuring sensor as set forth in claim 10 wherein said solid material is further defined as integrally formed with said window.

12. The measuring sensor as set forth in claim 10 wherein said solid material is in direct contact with said window.

13. The measuring sensor as set forth in claim 1 wherein said sample volume has windows at both of said ends, and wherein said sample volume is formed as a sample chamber.

14. The measuring sensor as set forth in claim 13 wherein said solid material is further defined as integrally formed with at least one of said windows.

15. The measuring sensor as set forth in claim 13 wherein said solid material is in direct contact with at least one of said windows.

16. The measuring sensor as set forth in claim 1 further including a wave tube (4d, 4e, 4f) along at least one of said first and second lengths (L2, L3), said wave tube comprising a sheath of material non-transmissive to radiation, said wave tube having a length (L4) which is at least substantially quintuple its mean diameter (D, DD), said wave tube having an internal space in which said solid material is positioned.

17. The measuring sensor as set forth in claim 1 wherein said solid material comprises a crystalline or amorphous material transmissive to infrared radiation.

18. The measuring sensor as set forth in claim 1 wherein said solid material comprises an arsenide, fluoride, bromide, chloride, iodide, selenide, sulfide, or oxide metal salt or combination or mixture thereof, silicon, silicate, glass, quartz, or germanium.

19. The measuring sensor as set forth in claim 1 wherein said solid material is further defined as being substantially homogenous in the direction of said radiation path (R), said solid Material having end surfaces that receive and emit radiation and having an additional surface not receiving or emitting radiation, said additional surface being treated to provide desired reflective properties to said additional surfaces.

20. A measuring sensor as set forth in claim 1 wherein at least one of said first and second lengths (L2, L3) is at least substantially 40% of said measuring absorption length (L1).

21. A measuring sensor as set forth in claim 1 wherein at least one of said first and second lengths (L2, L3) is at least one and a half times the length of said measuring absorption length (L1).

22. A measuring sensor as set forth in claim 21 wherein at least one of said first and second lengths (L2, L3) is at least substantially quintuple said measuring absorption length (L1).

23. A measuring sensor as set forth in claim 3 wherein said second length includes a beam distribution section (L4a) which is not more than 30% of the second length (L3).

24. A measuring sensor as set forth in claim 1 wherein said means interposed in said radiation path comprises an optical filter.

25. A measuring sensor as set forth in claim 1 wherein said means interposed in said radiation path comprises radiation dispersion producing means.

* * * * *

UNITED STATES PATENT AND TRADEMARK OFFICE
CERTIFICATE OF CORRECTION

PATENT NO. : 6,046,814
DATED : April 4, 2000
INVENTOR(S) : Kai Karlsson, et. al.

It is certified that error appears in the above-identified patent and that said Letters Patent is hereby corrected as shown below:

Column 11, line 42, delete "yet".

Signed and Sealed this

Eleventh Day of July, 2000

Attest:

Q. TODD DICKINSON

*Attesting Officer*          *Director of Patents and Trademarks*